US009033980B2

(12) United States Patent
Grimaldi

(10) Patent No.: US 9,033,980 B2
(45) Date of Patent: May 19, 2015

(54) CATHETER FOR PERCUTANEOUS TRANSCATHETER ABLATION OF CARDIAC ARRHYTHMIAS USING BIPOLAR RADIOFREQUENCY

(76) Inventor: Massimo Grimaldi, Bari (IT)

( * ) Notice: Subject to any disclaimer, the term of this patent is extended or adjusted under 35 U.S.C. 154(b) by 835 days.

(21) Appl. No.: 12/663,962

(22) PCT Filed: Jun. 13, 2008

(86) PCT No.: PCT/IT2008/000397
§ 371 (c)(1),
(2), (4) Date: Dec. 10, 2009

(87) PCT Pub. No.: WO2008/152674
PCT Pub. Date: Dec. 18, 2008

(65) Prior Publication Data
US 2010/0174280 A1 Jul. 8, 2010

(30) Foreign Application Priority Data
Jun. 14, 2007 (IT) .................. BA07A0049

(51) Int. Cl.
*A61B 18/18* (2006.01)
*A61B 18/14* (2006.01)
*A61B 18/00* (2006.01)
*A61M 25/00* (2006.01)

(52) U.S. Cl.
CPC ... *A61B 18/1492* (2013.01); *A61B 2018/00214* (2013.01); *A61B 2018/00839* (2013.01); *A61B 2018/1467* (2013.01); *A61M 25/007* (2013.01)

(58) Field of Classification Search
CPC ........... A61B 18/1492; A61B 2018/00351; A61B 2018/00589; A61B 2018/00577

USPC ............... 606/33, 40, 41, 50, 32, 48
See application file for complete search history.

(56) References Cited

U.S. PATENT DOCUMENTS

| 5,462,545 | A | * | 10/1995 | Wang et al. ............. 606/41 |
| 5,582,609 | A | * | 12/1996 | Swanson et al. ........ 606/39 |
| 5,584,830 | A | * | 12/1996 | Ladd et al. .............. 606/34 |
| 5,673,695 | A | * | 10/1997 | McGee et al. ........... 600/374 |
| 5,849,028 | A | * | 12/1998 | Chen ....................... 607/102 |
| 5,860,974 | A | * | 1/1999 | Abele ...................... 606/41 |
| 5,913,856 | A | * | 6/1999 | Chia et al. ............... 606/41 |
| 5,957,842 | A | * | 9/1999 | Littmann et al. ........ 600/381 |
| 6,017,338 | A | * | 1/2000 | Brucker et al. .......... 606/41 |
| 6,033,403 | A | * | 3/2000 | Tu et al. .................. 606/41 |
| 6,106,522 | A | * | 8/2000 | Fleischman et al. .... 606/41 |
| 6,475,213 | B1 | * | 11/2002 | Whayne et al. ......... 606/34 |
| 6,514,250 | B1 | * | 2/2003 | Jahns et al. ............. 606/41 |
| 6,595,991 | B2 | * | 7/2003 | Tollner et al. ........... 606/41 |
| 6,926,669 | B1 | * | 8/2005 | Stewart et al. .......... 600/439 |
| 8,123,742 | B2 | * | 2/2012 | Berger .................... 606/27 |
| 8,187,270 | B2 | * | 5/2012 | Auth et al. .............. 606/42 |
| 2001/0007070 | A1 | * | 7/2001 | Stewart et al. .......... 606/41 |
| 2001/0025175 | A1 | * | 9/2001 | Panescu et al. ......... 606/41 |

(Continued)

FOREIGN PATENT DOCUMENTS

WO 00/67656 11/2000

*Primary Examiner* — Joseph Stoklosa
*Assistant Examiner* — Jocelyn D Ram
(74) *Attorney, Agent, or Firm* — Lucas & Mercanti, LLP

(57) ABSTRACT

A catheter that distributes bipolar radiofrequency for use during the percutaneous ablation of cardiac arrhythmias. The catheter comprising a flexible sheath, a handle, a pull-wire, holes for irrigation in its distal tip, sensing means and electrodes.

5 Claims, 3 Drawing Sheets

(56) References Cited

U.S. PATENT DOCUMENTS

Figure 1:
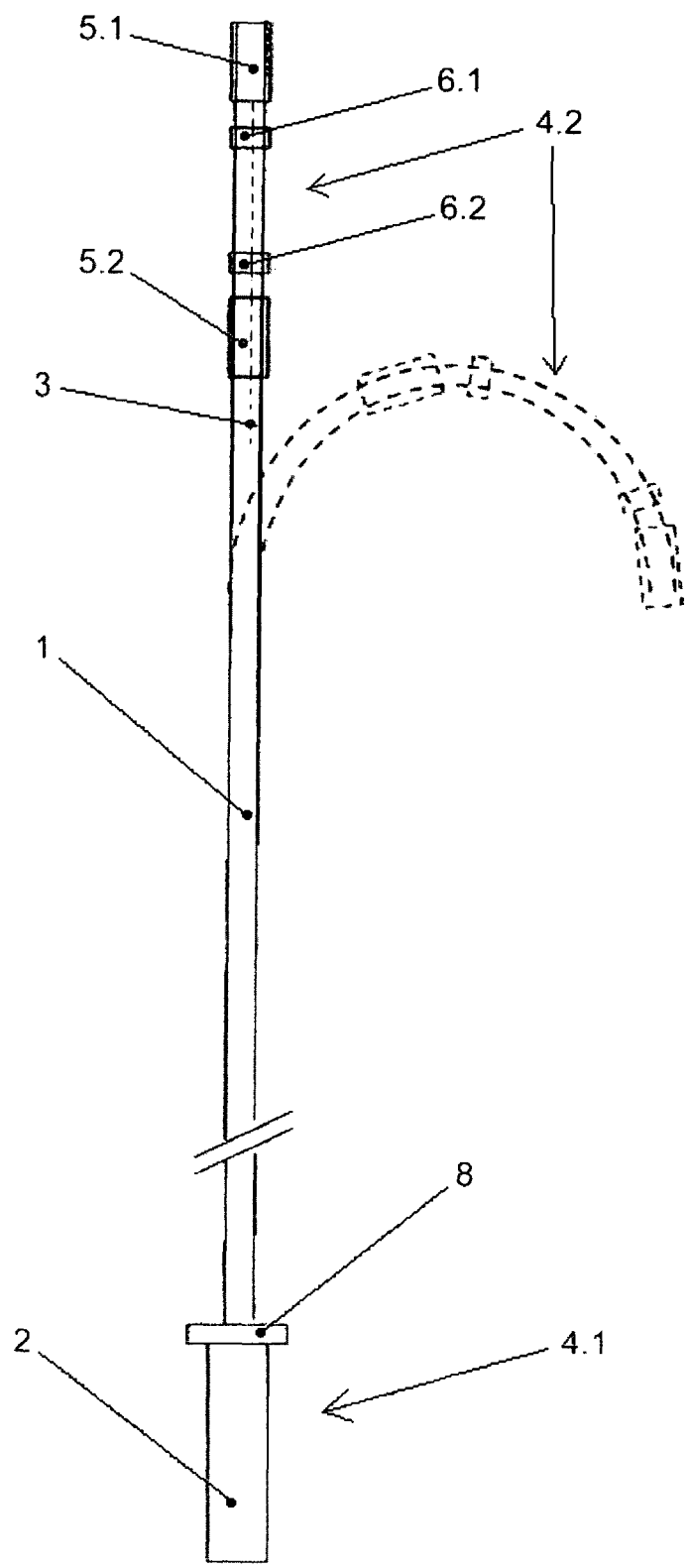

| | | |
|---|---|---|
| 2002/0032441 A1 | 3/2002 | Ingle et al. |
| 2002/0087208 A1 | 7/2002 | Koblish et al. |
| 2002/0123749 A1* | 9/2002 | Jain .................. 606/41 |
| 2002/0193790 A1* | 12/2002 | Fleischman et al. ........... 606/41 |
| 2003/0004505 A1* | 1/2003 | Bencini et al. .................. 606/41 |
| 2003/0088244 A1* | 5/2003 | Swanson et al. ............... 606/41 |
| 2003/0233090 A1 | 12/2003 | Whayne |
| 2004/0082948 A1* | 4/2004 | Stewart et al. .................. 606/41 |
| 2005/0015084 A1* | 1/2005 | Hill et al. ........................ 606/41 |
| 2006/0111704 A1 | 5/2006 | Brenneman |
| 2006/0241366 A1* | 10/2006 | Falwell et al. ................ 600/374 |
| 2010/0057074 A1* | 3/2010 | Roman et al. .................. 606/33 |
| 2012/0059255 A1* | 3/2012 | Paul et al. ..................... 600/431 |
| 2012/0078076 A1* | 3/2012 | Stewart et al. ................ 600/373 |

* cited by examiner

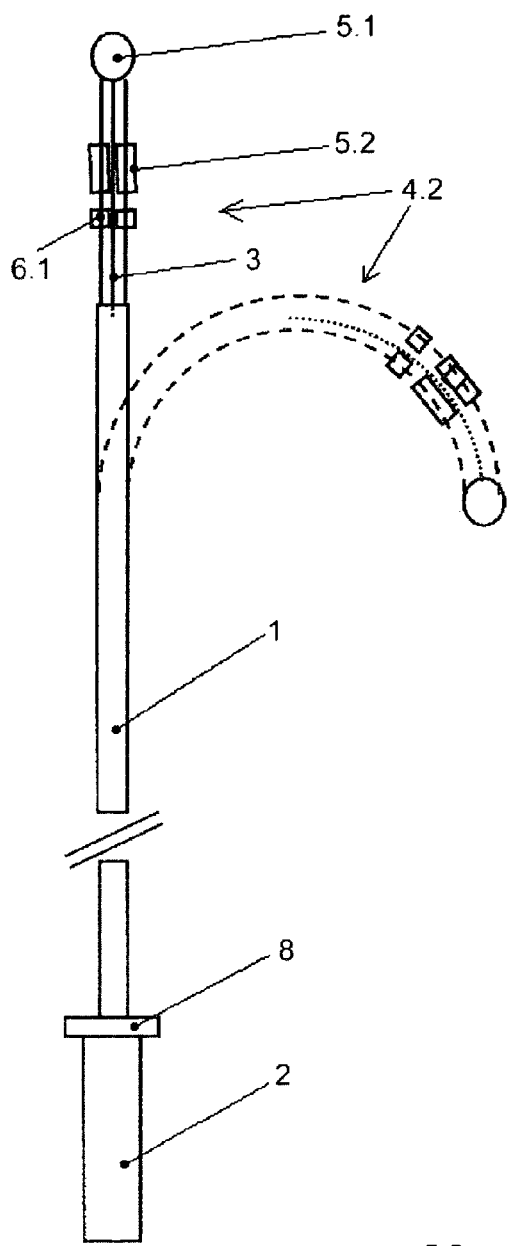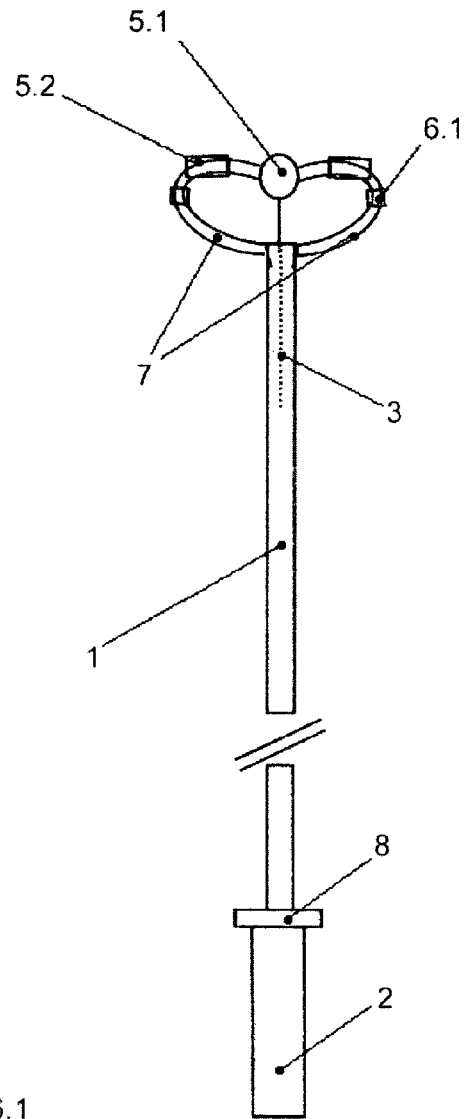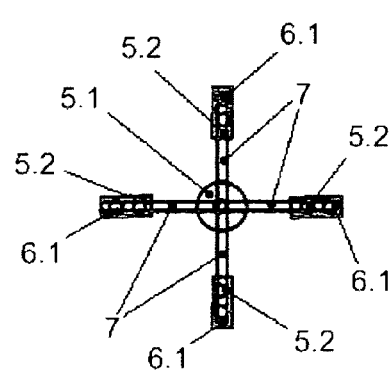
Fig. 2
Fig. 3
Fig. 4

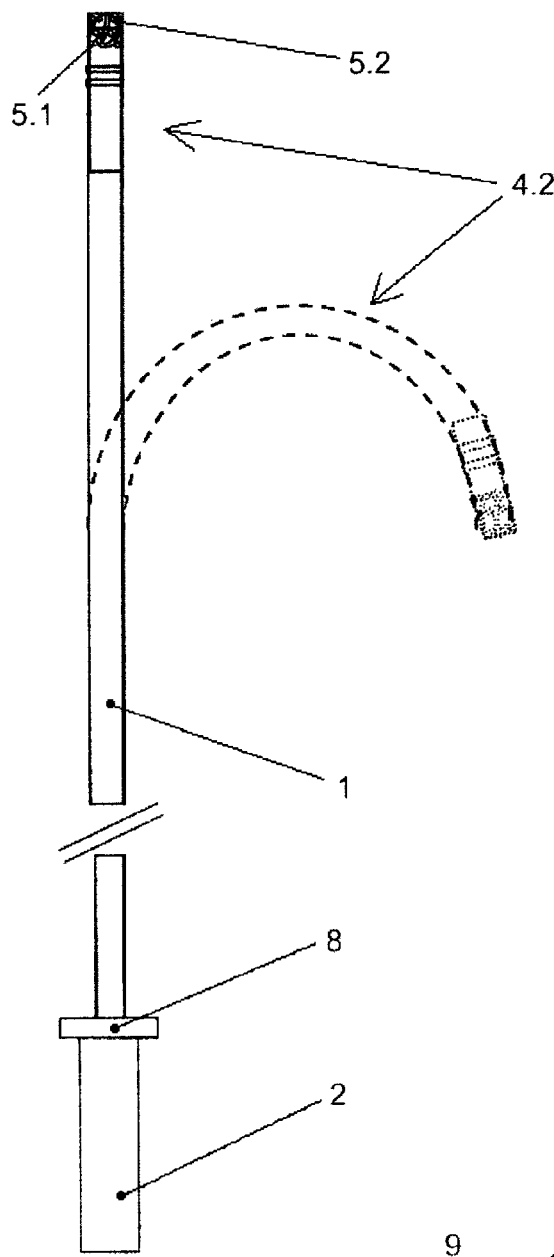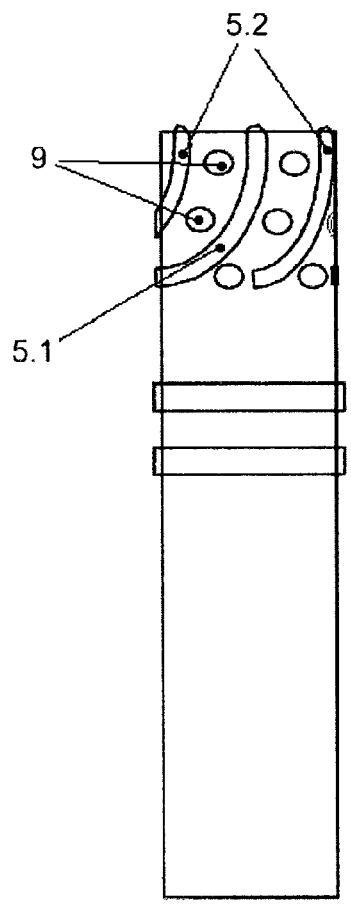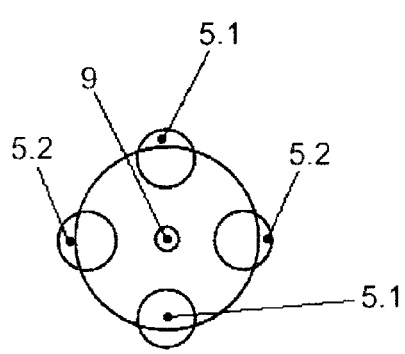
Fig. 5
Fig. 6
Fig. 7

CATHETER FOR PERCUTANEOUS TRANSCATHETER ABLATION OF CARDIAC ARRHYTHMIAS USING BIPOLAR RADIOFREQUENCY

This application is a 371 of PCT/IT2008/000397 filed on Jun. 13, 2008, which claims priority to and the benefit of Italian Application No. BA2007A000049 filed on Jun. 14, 2007, the contents of which are incorporated herein by reference.

This invention consists of a catheter that distributes bipolar radiofrequency for use during the percutaneous ablation of cardiac arrhythmias.

Transcatheter ablation of arrhythmias is an invasive cardiological technique which eliminates heartbeat disorders. This is achieved by eliminating arrhythmogenic tissue.

In the vast majority of cases this elimination is achieved through the distribution of unipolar radiofrequency through catheters introduced percutaneously.

The best known catheters, despite their differences from a mechanical and functional point of view, are all united by the fact that they only distribute unipolar radiofrequency.

The radiofrequency is distributed in correspondence with an electrode which is positioned on the tip of the catheter; the circuit is then closed on a conducting plaque which is usually applied to the patient's back.

This means that once distinguished the fractions of arrhythmogenic tissue to eliminate, ablation can be performed only in single points, creating minor discrete lesions.

This in turn means that the operation lasts a long time, particularly if the points of arrhythmogenic tissue are numerous and spread out.

In this case, where there are a large number of arrhythmogenic areas possibly closely packed in a limited section of tissue, it is normal practice to to perform a transmural lesion, which creates a circumscribed barrier isolating the interested part.

Therefore, instead of intervening singularly in every arrhythmia inducing point of the tissue, it is generally performed a comprehensive isolation of the whole interested tissue portion. Such a technique comports doubtless advantages either in time or in efficacy; the risk of missing any arrhythmogenic focus is drastically reduced.

However, the main disadvantage of this technique consists in the operative difficulty in tracing a linear and continuous lesion. For example in typical atria flutter ablation, creating a linear lesion in the cavotricuspidal isthmus by unipolar radiofrequency comports substantial technical difficulties, due to the elevated myocardial thickness or the presence of narrow recesses in this area of the heart.

The unipolar radiofrequency also compels the 'drawing' of the transmural lesion, being careful to maintain an appropriate and constant depth along the whole perimeter of the barrier being created.

The appropriate depth of the transmural lesion is to be emphatically taken into consideration as the efficiency of the barrier created or, viceversa, any serious complications that arise from the operation depend on the appropriate depth being maintained.

Among the more serious complications, and almost always fatal, is the atrial-oesophageal fistula. This complication is due to the closeness of the oesophagus to the left atrium. This means that lesions which are too deep can damage this delicate organ causing pain during the operation as well as the aforementioned fistula in the following weeks.

A further risk when using catheters with unipolar radiofrequencies is the formation of thrombi or the carbonisation of the blood.

The main aim of this invention is to provide a catheter for the ablation of cardiac arrhythmia that would lead to a significant reduction in operating time and an improvement in the efficiency of the procedure.

Another important aim is to provide a catheter with which it is possible to carry out transmural lesions rapidly and easily whilst also reducing the risk of complications.

In order to achieve these aims this invention solves the problem of obtaining a uniform linear transmural lesion which, besides what is stated above, reduces the risk of damaging nearby structures, carbonisation of blood and the formation of thrombi.

These and other aims are achieved by the catheter with bipolar radiofrequency used in this invention and described below in three preferred procedures, which are not intended to be limitative but are open to further development within the context of the invention. The descriptions are accompanied by the attached tables which illustrate the following figures:

FIG. 1) lateral view of the catheter in two positions with the tip straight and curved in a procedure with the poles aligned with the extremity of the flexible cable;

FIG. 2) the same view as FIG. 1), in a procedure with the tip with the four lateral electrodes and the pull-wire extracted;

FIG. 3) the same procedure as FIG. 2) the lateral view with the pull-wire retracted;

FIG. 4) view from above of the procedure in FIG. 2) with the pull-wire retracted;

FIG. 5) the same view as FIG. 1) in a procedure with the curved electrodes on the tip of the catheter:

FIG. 6) lateral view of a detail of the tip of the catheter in FIG. 5);

FIG. 7) view from above of the procedure in FIG. 5).

The catheter mentioned in this invention is formed by a flexible cable 1, whose extremity 4.1 is provided of a handle 2 with a plunger 8. The last is connected to a pull-wire 3 internal to the flexible cable 1. The pull wire 3 can bend the extremity 4.2 opposed to 4.1, whenever it is pulled back.

On the aforementioned extremity 4.2 the poles through which the distribution of radiofrequency takes place and through which information is gathered regarding the arrhythmia (sensing) are positioned.

The innovation introduced by this invention lies in providing the extremity 4.2 of the catheter with two external poles 5.1 and 5.2, one negative and one positive, through which a radiofrequency will be generated which produces a linear wave of lesion rather than punctiform.

Therefore a bipolar radiofrequency rather than unipolar radiofrequency is generated.

It therefore seems evident that the ability to produce a linear lesion which runs between the two poles 5.1 and 5.2 allows a complete and continuous transmural lesion to be carried out in just a few seconds which allows the perfect isolation of the section of tissue affected by cardiac arrhythmia.

Furthermore, in this way it becomes easier to carry out lesions in unstable areas or where there are narrow recesses or and increased thickness of the myocardium.

The atrial-oesophageal fistula, caused by the increase in temperature of the oesophagus during the ablation of the arrhythmia, would also be avoided by bipolar radiofrequency because the energy would be concentrated between the poles 5.1 and 5.2 on the catheter itself and therefore the lesion would not involve paracardiac structures.

In the procedure shown in FIG. 1 the two poles 5.1 and 5.2 are both positioned along the extremity 4.2 of the flexible cable 1 of the catheter lined up with each other.

The bipolar radiofrequency is distributed by the distal electrode 5.1 (negative pole) to the proximal pole 5.2 (positive pole).

Interposed with the two poles are two electrodes 6.1 and 6.2 which form an electric dipole with the poles 5.1 and 5.2 respectively and which are exclusively for so-called 'sensing', that is the gathering of information regarding the arrhythmias (for example precocity and morphology).

In the procedure in FIG. 2) the catheter makes use of a spherical distal electrode 5.1, positioned at the tip, which represents the negative pole, and four proximal electrodes 5.2 with a semi-circular shape which represent the positive poles for the distribution of the bipolar radiofrequency.

The aforementioned electrodes 5.2, with the pull-wire open, are positioned laterally on the flexible cable 1 and permit a wave of lesion the same as that described in the previous procedure.

Retracting the pull-wire 3 the catheter assumes the configuration shown in FIG. 3) and permits four "wings" (FIG. 4) which are reciprocally perpendicular, each with a distributing electrode 5.2 and a smaller electrode 6.1 for 'sensing' (which closes the dipole with the nearby distributing electrode).

The wave of lesion is created between the negative central spherical electrode 5.1 and the positive electrodes 5.2 on the wing 7, each of which closes the circuit with the electrode 5.1 independently from the others.

In this procedure the radiofrequency can, in fact, be distributed by one or more electrodes contemporarily and selected, for example, via a dedicated switch box.

The catheter in FIG. 5) shows the distributing electrodes in a curved position to obtain complete lesions in any area of contact between the tip of the catheter and the tissue.

The four curve electrodes positioned on the lateral surface of the catheter's tip are made up of the two negative poles 5.2 and the positive poles 5.1 in alternate positions; both the two positive and the two negative poles are then united internally in the catheter.

The radiofrequency is distributed by each of the two negative poles 5.2 to the respective positive pole 5.1.

In each operation the catheter requires irrigation (9) of the distributing electrodes in order to reduce the local temperature as well as to permit a better transfer of radiofrequency in the tissue and to reduce the risk of the formation of thrombi or carbonisation of the blood.

The invention claimed is:

1. A transcatheter for percutaneous transcatheter ablation of cardiac arrhythmias using bipolar radiofrequency consisting of:
   a flexible cable having a proximal extremity and a distal extremity with respect to a handle,
      the handle having a plunger which operates a single pull-wire coaxial inside the flexible cable, said single pull-wire extending from the proximal extremity to the distal extremity such that when the single pull-wire is pulled back the distal extremity is bent, said plunger having a circular shape and a diameter greater than the handle,
      the distal extremity having irrigation holes for irrigation and a first and a second arrhythmias sensing electrodes for gathering information regarding arrhythmias,
   a distal electrode and a proximal electrode,
      the distal and proximal electrodes being one negative and one positive and positioned on the external surface of the flexible cable of the transcatheter, for generating a bipolar radiofrequency that creates a wave of lesion that goes from the distal electrode to the proximal electrode,
   wherein the first and the second arrhythmias sensing electrodes are disposed in close proximity to the distal and proximal electrodes in order to form an electric dipole with the distal electrode and another electric dipole with the proximal electrode.

2. The transcatheter for ablation as claimed in claim 1, wherein the distal electrode and the proximal electrode are both positioned along the distal extremity on the external lateral surface of the flexible cable of the transcatheter, lined up with each other, thereby distributing the bipolar radiofrequency from the distal electrode to the proximal electrode.

3. The transcatheter of claim 1, wherein the first and the second arrhythmias sensing electrodes are interposed between the distal and proximal electrodes.

4. A transcatheter for percutaneous transcatheter ablation of cardiac arrhythmias using bipolar radiofrequency consisting of:
   a flexible cable having a proximal extremity and a distal extremity, the distal extremity having irrigation holes for irrigation and a first and a second arrhythmias sensing electrodes for gathering information regarding arrhythmias;
   a handle on the proximal extremity, the handle having a plunger operating a single pull-wire coaxial inside the flexible cable, said single pull-wire extending from the proximal extremity to the distal extremity such that when the single pull-wire is pulled back the distal extremity is bent, said plunger having a circular shape and a diameter greater than the handle; and
   a plurality of pairs of a distal electrode and a proximal electrode, the distal and proximal electrodes being one negative and one positive, contemporarily positioned on the external surface of the transcatheter, for generating a bipolar radiofrequency that creates a wave of lesion that goes from the distal electrode to the proximal electrode, wherein the choice of the pairs of the distal and proximal electrodes can be carried out via an external switch box,
   wherein the first and the second arrhythmias sensing electrodes are disposed in close proximity to the distal and proximal electrodes in order to form an electric dipole with the distal electrode and another electric dipole with the proximal electrode.

5. The transcatheter of claim 4, wherein the first and the second arrhythmias sensing electrodes are interposed between the distal and proximal electrodes.

* * * * *